(12) United States Patent
Ishii et al.

(10) Patent No.: US 6,323,346 B1
(45) Date of Patent: Nov. 27, 2001

(54) PROCESS FOR PRODUCING AZIRIDINE COMPOUNDS

(75) Inventors: Yasutaka Ishii, Takatsuki; Tatsuya Nakano, Himeji, both of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/522,072

(22) Filed: Mar. 9, 2000

(30) Foreign Application Priority Data

Mar. 9, 1999 (JP) .................................................. 11-062442

(51) Int. Cl.⁷ ...................... C07D 203/08; C07D 203/10; C07D 203/12; C07D 205/05
(52) U.S. Cl. ........................... 548/954; 548/967; 548/968; 558/434
(58) Field of Search ................................... 548/954, 967, 548/968; 558/434

(56) References Cited

FOREIGN PATENT DOCUMENTS

01157952A2 * 6/1989 (JP) .

OTHER PUBLICATIONS

Mayer, M. et al, J. Org. Chem., 1998, XP000910084, vol. 63, pp. 6839–6844.
Mohan, J. et al, Chem. Commun., 1997, XP–002051266, pp. 1429–1430.
Casarrubios L., et al, J. Org. Chem., 1996, XP00915529, pp. 8358–8359.
Zhu, Z. et al, J. Org. Chem., 1995, XP000910037, pp. 7090–7091.
Rasmussen, K. G. et al, J. Chem. Soc., 1977, XP000910026, pp. 1287–1291.
Rasmussen, K. G. et al, J. Chem. Soc., 1995, XP000910041, pp. 1401–1402.

* cited by examiner

Primary Examiner—T. A. Solola
(74) Attorney, Agent, or Firm—Birch, Stewart, Kolasch, & Birch, LLP

(57) ABSTRACT

In the presence of an iridium compound, an imine of the following formula (1):

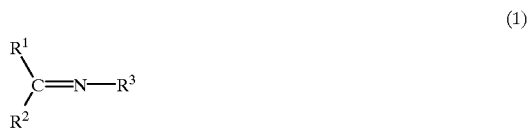

(1)

wherein $R^1$, $R^2$ and $R^3$ are each, identical to or different from one another, a hydrogen atom or a non-reactive organic group, where $R^1$ and $R^2$ may be combined to form a ring together with the adjacent carbon atom, is reacted with a diazoacetic acid derivative of the following formula (2):

$$N_2CHR^4 \quad (2)$$

wherein $R^4$ is a cyano group, an alkoxycarbonyl group, a carbamoyl group or the like, to yield an aziridine compound of the following formula (5):

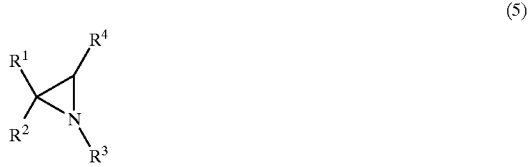

(5)

wherein $R^1$, $R^2$, $R^3$ and $R^4$ have the same meanings as defined above. The process can easily and efficiently produce aziridine compounds.

6 Claims, No Drawings

PROCESS FOR PRODUCING AZIRIDINE COMPOUNDS

BACKGROUND OF THE INVENTION

1. Field of the Invention

The present invention relates to a process for producing aziridine compounds which are useful as, for example, precursors of amino acids and β-lactam antibiotics and as intermediates in organic synthetic reactions.

2. Description of the Related Art

Processes are known for producing aziridine compounds. For example, such aziridine compounds can be obtained by (i) a process of allowing a halogenating agent such as phosphorus chloride or thionyl chloride to act on a β-amino-alcohol to form a β-halogenoamine and treating the β-halogenoamine with potassium hydroxide or another base for cyclization (Gabriel method), (ii) a process of allowing sulfuric acid to act on aβ-amino-alcohol to form a β-amino-sulfuricester and reacting the β-amino-sulfuric ester with sodium hydroxide or another base for cyclization (Wenker method), or (iii) a process of reacting a ketoxime with a Grignard reagent in excess to form aziridine via azirine. These processes, however, require large amounts of phosphorus compounds or other reagents and are inevitably accompanied with complicated aftertreatments. In addition, the processes by-produce large amounts of salts, which are disadvantageous from viewpoints of resources and environment.

SUMMARY OF THE INVENTION

Accordingly, an object of the invention is to provide a process for easily and efficiently producing an aziridine compound.

After intensive investigations, the present inventors found that a reaction of an imine with a diazoacetic acid derivative in the presence of an iridium compound can produce a corresponding aziridine compound in good yield. The present invention has been accomplished on the basis of these findings.

Specifically, the invention provides, in an aspect, a process for producing an aziridine compound. The process includes the step of reacting an imine with a diazoacetic acid derivative in the presence of an iridium compound to yield an aziridine compound, and the imine is of the following formula (1):

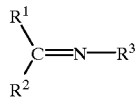
(1)

wherein $R^1$, $R^2$ and $R^3$ are each, identical to or different from one another, a hydrogen atom or a non-reactive organic group, where $R^1$ and $R^2$ may be combined to form a ring together with the adjacent carbon atom, the diazoacetic acid derivative is of the following formula (2):

$$N_2CHR^4 \quad (2)$$

wherein $R^4$ is a cyano group or a group of the following formula (3) or (4):

(3)

(4)

wherein $R^5$ is a hydrocarbon group or a heterocyclic group, and $R^6$ and $R^7$ are each, identical to or different from each other, a hydrogen atom, a hydrocarbon group or a heterocyclic group, where $R^6$ and $R^7$ may be combined to form a ring together with the adjacent nitrogen atom, and the aziridine compound is of the following formula (5):

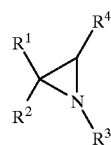
(5)

wherein $R^1$, $R^2$, $R^3$ and $R^4$ have the same meanings as defined above.

In another aspect, the invention provides another process for producing an aziridine compound. This process includes the step of reacting a carbonyl compound with an amino-group-containing compound and a diazoacetic acid derivative in the presence of an iridium compound to yield an aziridine compound of the formula (5). In this process, the carbonyl compound is of the following formula (6):

(6)

wherein $R^1$ and $R^2$ are each, identical to or different from each other, a hydrogen atom or a non-reactive organic group, where $R^1$ and $R^2$ may be combined to form a ring together with the adjacent carbon atom, the amino-group-containing compound is of the following formula (7):

$$R^3NH_2 \quad (7)$$

wherein $R^3$ is a hydrogen atom or a non-reactive organic group, and the diazoacetic acid derivative is of the following formula (2):

$$N_2CHR^4 \quad (2)$$

wherein $R^4$ is a cyano group or a group of the following formula (3) or (4):

(3)

(4)

wherein $R^5$ is a hydrocarbon group or a heterocyclic group, and $R^6$ and $R^7$ are each, identical to or different from each other, a hydrogen atom, a hydrocarbon group or a heterocyclic group, where $R^6$ and $R^7$ may be combined to form a ring together with the adjacent nitrogen atom.

DESCRIPTION OF THE PREFERRED EMBODIMENT

[Iridium Compound]

Iridium compounds (including elementary iridium) are employed as catalysts in the invention. Such iridium compounds include, but are not limited to, metallic iridium, iridium oxide, iridium sulfide, iridium hydroxide, iridium fluoride, iridium chloride, iridium bromide, iridium iodide, iridium sulfate, iridic acid or its salts (e.g., potassium iridate), inorganic iridium complexes [e.g., hexaammineiridium(III) salts, and pentaamminechloroiridium(III) salts], and other inorganic compounds; iridium cyanide, organic iridium complexes [e.g., tris(acetylacetonato)iridium, dodecacarbonyltetrairidium(0), chlorotricarbonyliridium(I), di-,μ-chlorotetrakis(cyclooctene)diiridium(I), di-μ-chlorotetrakis(ethylene)diiridium(I), di-[-chlorobis(1,5-cyclooctadiene)diiridium(I), di-,μ-chlorodichlorobis(pentamethylcyclopentadienyl)diiridium(III), trichlorotris(triethylphosphine)iridium(III), pentahydridobis(trimethylphosphine)iridium(V), chlorocarbonylbis(triphenylphosphine)iridium(I), chloroethylenebis(triphenylphosphine)iridium(I), (pentamethylcyclopentadienyl)dicarbonyliridium(I), bis{1,2-bis(diphenylphosphino)ethane}iridium(I) chloride, pentamethylcyclopentadienylbis(ethylene)iridium(I), and carbonylmethylbis(triphenylphosphine)iridium(I)], and other organic compounds.

The iridium may have any valency ranging from 0 to 6, preferably from 0 to 3, and especially 1 or 3.

Preferred iridium compounds include iridium complexes, particularly organic iridium complexes. Among them, organic iridium complexes each having an unsaturated hydrocarbon ligand such as cyclooctene, 1,5-cyclooctadiene, ethylene, or pentamethylcyclopentadiene are typically preferred. Such organic iridium complexes include, but are not limited to, di-μ-chlorotetrakis(cyclooctene)diiridium(I), di -μ-chlorotetrakis(ethylene)diiridium(I), and di-μ-chlorobis(1,5-cyclooctadiene)diiridium(I). Each of these iridium compounds can be used alone or in combination.

The iridium compound can be employed as such or as being supported by a carrier. Such carriers include, for example, silica, alumina, silica-alumina, zeolite, titania, magnesia, and other inorganic metallic oxides, and activated carbon, and other conventional carriers for supporting catalysts. When the iridium compound is supported by a carrier, the proportion of the iridium compound is, for example, about 0.1 to 50% by weight, and preferably about 1 to 20% by weight relative to the weight of the carrier. The catalyst can be supported by the carrier in a conventional manner such as impregnation, precipitation, ion exchange, or another technique.

The amount of the iridium compound is, for example, about 0.001 to 1 mole, preferably about 0.005 to 0.3 mole, and more preferably about 0.01 to 0.1 mole relative to 1 mole of the substrate imine (or amino-group-containing compound).

[Imine]

The imines of the formula (1) for use as a reactant (substrate) include aldimines derived from aldehydes and ketimines derived from ketones. The term "imine" used herein also includes hydrazones, oximes, oxime ethers, oxime esters, and other compounds, as far as they each have a carbon-nitrogen double bond.

The non-reactive organic groups in $R^1$, $R^2$ and $R^3$ of the formula (1) have only to be non-reactive in the present reaction. The substituents $R^1$ and $R^2$ include, for example, hydrocarbon groups, heterocyclic groups, ester groups, amido groups, and a cyano group. Examples of $R^3$ include, in addition to these groups, a hydroxyl group, substituted oxy groups, and unsubstituted or N-substituted amino groups.

The hydrocarbon groups include aliphatic hydrocarbon groups, alicyclic hydrocarbon groups, aromatic hydrocarbon groups, and groups comprising these groups bonded with one another. Such aliphatic hydrocarbon groups include, but are not limited to, methyl, ethyl, propyl, isopropyl, butyl, isobutyl, s-butyl, t-butyl, pentyl, hexyl, decyl, dodecyl, and other alkyl groups each having about 1 to 20 (preferably about 1 to 10) carbon atoms; vinyl, allyl, 1-butenyl, and other alkenyl groups each having about 2 to 20 (preferably about 2 to 10) carbon atoms; ethynyl, propynyl, and other alkynyl groups each having about 2 to 20 (preferably about 2 to 10) carbon atoms.

The alicyclic hydrocarbon groups include, but are not limited to, cyclopropyl, cyclobutyl, cyclopentyl, cyclohexyl, cyclooctyl, and other cycloalkyl groups each having about 3 to 20 (preferably about 3 to 15, and more preferably about 5 to 8) members; and cyclopentenyl, cyclohexenyl, and other cycloalkenyl groups each having about 3 to 20 (preferably about 3 to 15, and more preferably about 5 to 8) members. Examples of the aromatic hydrocarbon groups are phenyl, naphthyl, and other aromatic hydrocarbon groups each having about 6 to 14 (preferably about 6 to 10) carbon atoms.

Hydrocarbon groups comprising an aliphatic hydrocarbon group and an alicyclic hydrocarbon group bonded with each other include, for example, cyclopentylmethyl, cyclohexylmethyl, 2-cyclohexylethyl, and other cycloalkyl-alkyl groups (e.g., $C_3$–$C_{20}$ cycloalkyl-$C_1$–$C_4$ alkyl groups). Hydrocarbon groups comprising an aliphatic hydrocarbon group and an aromatic hydrocarbon group bonded with each other include, but are not limited to, aralkyl groups (e.g., $C_7$–$C_{18}$ aralkyl groups), and alkyl-substituted aryl groups (e.g., phenyl or naphthyl group substituted with about one to four $C_1$–$C_4$ alkyl groups)

Examples of preferred hydrocarbon groups include $C_1$–$C_{10}$ alkyl groups, $C_2$–$C_{10}$ alkenyl groups, $C_2$–$C_{10}$ alkynyl groups, $C_3$–$C_{15}$ cycloalkyl groups, $C_6$–$C_{10}$ aromatic hydrocarbon groups, $C_3$–$C_{15}$ cycloalkyl-$C_1$–$C_4$ alkyl groups, and $C_7$–$C_{14}$ aralkyl groups.

The hydrocarbon groups may have a variety of substituents. Such substituents include, but are not limited to, halogen atoms, an oxo group, a hydroxyl group, substituted oxy groups (e.g., alkoxy groups, aryloxy groups, aralkyloxy groups, and acyloxy groups), a carboxyl group, substituted oxycarbonyl groups, substituted or unsubstituted carbamoyl groups, a cyano group, a nitro group, substituted or unsubstituted amino groups, and heterocyclic groups.

Heterocyclic rings constituting the heterocyclic groups include aromatic heterocyclic rings and non-aromatic heterocyclic rings. Such heterocyclic rings include, but are not limited to, heterocyclic rings each containing an oxygen atom as a hetero atom (e.g., furan, tetrahydrofuran, oxazole, isoxazole, and other 5-membered rings; 4-oxo-4H-pyran, tetrahydropyran, morpholine, and other 6-membered rings; benzofuran, isobenzofuran, 4-oxo-4H-chromene, chroman, isochroman, and other condensed rings), heterocyclic rings each containing a sulfur atom as a hetero atom (e.g., thiophene, thiazole, isothiazole, thiadiazole, and other 5-membered rings; 4-oxo-4H-thiopyran, and other 6-membered rings; benzothiophene and other condensed rings), and heterocyclic rings each containing a nitrogen atom as a hetero atom (e.g., pyrrole, pyrrolidine, pyrazole, imidazole, triazole, and other 5-membered rings; pyridine, pyridazine, pyrimidine, pyrazine, piperidine, piperazine, and other 6-membered rings; indole, indoline, quinoline, acridine, naphthyridine, quinazoline, purine, and other condensed rings). The heterocyclic groups may each have a substituent. Such substituents include, in addition to the aforementioned substituents which the hydrocarbon groups may have, alkyl groups (e.g., methyl, ethyl, and other $C_1$–$C_4$ alkyl groups), cycloalkyl groups, and aryl groups (e.g., phenyl, and naphthyl groups).

The ester groups include, but are not limited to, methoxycarbonyl, ethoxycarbonyl, and other alkoxycarbonyl groups, phenoxycarbonyl group, and other aryloxycarbonyl groups, cyclohexyloxycarbonyl group, and other cycloalkyloxycarbonyl groups. The amido groups include, for example, carbamoyl group, N,N-dimethylcarbamoyl group, and other N-substituted carbamoyl groups.

Rings which may be formed by $R^1$ and $R^2$ combined together with the adjacent carbon atom include, but are not limited to, cyclobutane, cyclopentane, cyclohexane, cyclohexene, cyclooctane, cyclododecane, and other non-aromatic carbocyclic rings (cycloalkane rings and cycloalkene rings) each having about 3 to 20 (preferably about 3 to 15, and more preferably about 5 to 12) members; oxolane, oxane, azolidine, perhydroazine, thiolane, thiane, and other non-aromatic heterocyclic rings each having about 3 to 20 (preferably about 3 to 12, and more preferably about 3 to 8) members. These rings may have any of the aforementioned substituents. Another ring (a non-aromatic or aromatic ring) may be condensed to these rings.

Preferred substituents $R^1$, $R^2$ and $R^3$ include a hydrogen atom and hydrocarbon groups, particularly a hydrogen atom, $C_1$–$C_{10}$ alkyl groups, $C_2$–$C_{10}$ alkenyl groups, $C_2$–$C_{10}$, alkynyl groups, $C_3$–$C_{15}$ cycloalkyl groups, $C_6$–$C_{10}$ aromatic hydrocarbon groups, $C_3$–$C_{12}$ cycloalkyl-$C_1$–$C_4$ alkyl groups, and $C_7$–$C_{14}$ aralkyl groups. Alternatively, the groups $R^1$ and $R^2$ may be preferably combined together with the adjacent carbon atom to form a non-aromatic carbocyclic ring or a non-aromatic heterocyclic ring each having about 3 to 20 members. In a typically preferred embodiment of the invention, at least one of $R^1$ and $R^2$ is a hydrogen atom.

Typical examples of the imines of the formula (1) include N-methylidenebutylamine, N-ethylideneamine, N-ethylidenemethylamine, N-ethylideneethylamine, N-ethylidenepropylamine, N-ethylidenebutylamine, N-ethylidenehexylamine, N-ethylidenebenzylamine, N-ethylideneaniline, N-propylideneethylamine, N-propylidenebenzylamine, N-propylideneaniline, N-butylidenebutylamine, N-butylidene-sec-butylamine, N-butylidene-tert-butylamine, N-butylidene-benzylamine, N-butylidene-aniline, 2-methylpropylidenebutylamine, N-(3-pyridylmethylidene)butylamine, N-(2-furylmethylidene)butylamine, N-butylidene(3-pyridylamine), 3-phenylpropylidenepropylamine, N-benzylidenebutylamine, and other aldimines; N-(1-methylethylidene)butylamine, N -(1-methylethylidene)benzylamine, N-(1-methylethylidene)aniline, N-(1-methylbutylidene)butylamine, N-(l-phenylethylidene)butylamine, and other ketimines.

The imines of the formula (1) can be obtained by subjecting a carbonyl compound of the formula (6) and an amino-group-containing compound of the formula (7) described below to dehydration-condensation in a conventional manner.

[Carbonyl Compound and Amino-group-containing Compound]

In the present invention, a combination of a corresponding carbonyl compound of the formula (6) with an amino-group-containing compound of the formula (7) can be employed as reactants instead of the imine of the formula (1). The term "amino-group-containing compound" used herein also includes ammonia.

The substituents $R^1$, $R^2$ and $R^3$ in the formulae (6) and (7) include groups similar to those as exemplified above. Typical examples of the carbonyl compounds of the formula (6) are formaldehyde, acetaldehyde, propionaldehyde, butyraldehyde, isobutyraldehyde, pentanal, hexanal, decanal, acrolein (acrylaldehyde), crotonaldehyde, and other aliphatic aldehydes; cyclohexanecarbaldehyde, and other alicyclic aldehydes; benzaldehyde, cinnamaldehyde, and other aromatic aldehydes; furfural, and other heterocyclic aldehydes; acetone, ethyl methyl ketone, diethyl ketone, isobutyl methyl ketone, and other aliphatic ketones; cyclopentanone, cyclohexanone, and other alicyclic ketones; acetophenone, propiophenone, and other aromatic ketones; and 2-acetofuron, and other heterocyclic ketones.

The amino-group-containing compounds of the formula (7) include, but are not limited to, ammonia; methylamine, ethylamine, propylamine, butylamine, isobutylamine, sec-butylamine, tert-butylamine, pentylamine, hexylamine, decylamine, and other aliphatic primary amines; cyclohexylamine, and other alicyclic primary amines; benzylamine, aniline, toluidine, and other aromatic primary amines; and hydroxylamine, o-methylhydroxylamine, hydrazine, and N,N-dimethylhydrazine.

The proportion (molar ratio) of the carbonyl compound to the amino-group-containing compound is such that the former/the latter is about 3/1 to 1/3, preferably about 2/1 to 1/2, more preferably about 1.5/1 to 1/1.5, and particularly about 1.2/1 to 1/1.2. The process using the carbonyl compound and the amino-group-containing compound as reactants is greatly advantageous in that the process requires no synthesis of an imine out of the system in advance and can produce a variety of corresponding aziridines from substrates that are easily available.

[Diazoacetic Acid Derivative]

The diazoacetic acid derivatives of the formula (2) include diazoacetonitrile, diazoacetic esters, and diazoacetic acid amides. The group $R^4$ in the formula (2) is a cyano group or a group of the following formula (3) or (4):

—COOR⁵             (3)

—CONR⁶R⁷            (4)

wherein $R^5$ is a hydrocarbon group or a heterocyclic group, and $R^6$ and $R^7$ are each, identical to or different from each other, a hydrogen atom, a hydrocarbon group or a heterocyclic group, where $R^6$ and $R^7$ may be combined to form a ring together with the adjacent nitrogen atom.

Hydrocarbon groups and heterocyclic groups in $R^5$, $R^6$, and $R^7$ include groups similar to those as exemplified in $R^1$ and the like. Rings formed by $R^6$ and $R^7$ combined together with the adjacent nitrogen atom include, for example, aziridine ring, pyrrolidine ring, piperidine ring, morpholine ring, piperazine ring, and other nitrogen-containing heterocyclic rings each having about 3 to 8 members.

Preferred substituent $R^5$ includes hydrocarbon groups, particularly $C_1$–$C_{10}$ alkyl groups, $C_2$–$C_{10}$ alkenyl groups, $C_2$–$C_{10}$ alkynyl groups, $C_3$–$C_{15}$ cycloalkyl groups, $C_6$–$C_{10}$ aromatic hydrocarbon groups, $C_3$–$C_{12}$ cycloalkyl-$C_1$–$C_4$ alkyl groups, and $C_7$–$C_{14}$ aralkyl groups. Among them, $C_1$–$C_4$ alkyl groups, $C_2$–$C_4$ alkenyl groups, and $C_6$–$C_{10}$ aromatic hydrocarbon groups are typically preferred as $R^5$.

Preferred substituents $R^6$ and $R^7$ include a hydrogen atom and hydrocarbon groups, particularly a hydrogen atom, $C_1$–$C_{10}$ alkyl groups, $C_2$–$C_{10}$ alkenyl groups, $C_2$–$C_{10}$ alkynyl groups, $C_3$–$C_{15}$ cycloalkyl groups, $C_6$–$C_{10}$ aromatic hydrocarbon groups, $C_3$–$C_{12}$ cycloalkyl-$C_1$–$C_4$ alkyl groups, and $C_7$–$C_{14}$ aralkyl groups. Among them, $C_1$–$C_4$ alkyl groups, $C_2$–$C_4$ alkenyl groups, and $C_6$–$C_{10}$ aromatic hydrocarbon groups are typically desirable as $R^6$ and $R^7$. Alternatively, $R^6$ and $R^7$ may be preferably combined together with the adjacent nitrogen atom to form a nitrogen-containing heterocyclic ring having about 3 to 8 members.

Typical examples of the diazoacetic acid derivatives include, but are not limited to, diazoacetonitrile; methyl diazoacetate, ethyl diazoacetate, propyl diazoacetate, isopropyl diazoacetate, allyl diazoacetate, phenyl diazoacetate, and other diazoacetic esters; diazoacetamide, N-methyldiazoacetamide, N,N-dimethyldiazoacetamide, and other diazoacetic acid amides.

The amount of the diazoacetic acid derivative is, for example, about 0.5 to 5 moles, preferably about 0.8 to 3 moles, and more preferably about 1.5 to 2.5 moles relative to 1 mole of the imine (or the amino-group-containing compound).

[Reaction]

A reaction is performed in the presence of, or in the absence of, a solvent. Such solvents include, but are not limited to, hexane, heptane, octane, and other aliphatic hydrocarbons; cyclohexane, and other alicyclic hydrocarbons; benzene, toluene, xylene, ethylbenzene, and other aromatic hydrocarbons; chloroform, dichloromethane, 1,2-dichloroethane, and other halogenated hydrocarbons; diethyl ether, dimethoxyethane, tetrahydrofuran, dioxane, and other ethers; methanol, ethanol, and other alcohols; acetone, ethyl methyl ketone, and other ketones; methyl acetate, ethyl acetate, isopropyl acetate, butyl acetate, and other esters; N,N-dimethylformamide, N,N-dimethylacetamide, and other amides; acetonitrile, propiononitrile, benzonitrile, and other nitriles; and acetic acid, and other organic acids. Each of these solvents can be used alone or in combination.

When the carbonyl compound and the amino-group-containing compound are used as reactants, the presence of a conventional dehydrating agent in the reaction system for removing by-produced water can advantageously proceed the reaction. Such dehydrating agents include, for example, Molecular Sieve 4A, Molecular Sieve 5A, and other molecular sieves.

A reaction temperature can be selected appropriately according to the species of the substrate and catalyst, and is, for example, about –20° C. to +150° C., preferably about –20° C. to +100° C., and more preferably about –10° C. to +50° C. The reaction can be performed either under atmospheric pressures or under pressure, in any system such as a batch system, a semi-batch system or a continuous system.

According to the invented processes, the reaction can produce the aziridine compounds of the formula (5) in good yields under mild conditions. Depending on the conditions, dimerization of the diazoacetic acid derivative may proceed to by-produce a fumaric acid derivative or a maleic acid derivative of the following formula (8):

$$R^4CH=CHR^4 \qquad (8)$$

wherein $R^4$ has the same meaning as defined above.

After the completion of the reaction, reaction products can be easily separated and purified in a conventional manner such as filtration, concentration, distillation, extraction, crystallization, recrystallization, column chromatography and other separation means, or any combination of these separation means.

As described above, the invented processes can easily and efficiently produce aziridine derivatives.

The present invention will now be illustrated in more detail with reference to several inventive examples below, which are not intended to limit the scope of the invention. In the examples, reaction products were analyzed by gas chromatography.

EXAMPLE 1

A mixture of 0.5 mmol of N-butylidenebutylamine, 0.5 mmol of ethyl diazoacetate, 0.015 mmol of di-μ-chlorotetrakis(cyclooctene)diiridium(I) [$Ir_2Cl_2$(cyclooctene)$_4$], and 0.5 ml of tetrahydrofuran was stirred at room temperature (25° C.) in an argon atmosphere for 3 hours. As a result, 1-butyl-2-ethoxycarbonyl-3-propylaziridine was obtained in a yield of 29%. Small amounts of diethyl fumarate and diethyl maleate were formed as by-products.

EXAMPLE 2

A mixture of 0.5 mmol of N-butylidenebutylamine, 0.5 mmol of ethyl diazoacetate, 0.015 mmol of di-μ-chlorotetrakis(cyclooctene)diiridium(I) [$Ir_2Cl_2$(cyclooctene)$_4$], and 0.5 ml of ethanol was stirred at room temperature (250° C.) in an argon atmosphere for 3 hours to yield 1-butyl-2-ethoxycarbonyl-3-propylaziridine in a yield of 30%.

EXAMPLE 3

A mixture of 0.5 mmol of N-butylidenebutylamine, 0.5 mmol of ethyl diazoacetate, 0.015 mmol of di-μ-chlorotetrakis(cyclooctene)diiridium(I) [$Ir_2Cl_2$(cyclooctene)$_4$], and 0.5 ml of 1,2-dichloroethane was stirred at room temperature (25° C.) in an argon atmosphere for 3 hours to yield 1-butyl-2-ethoxycarbonyl-3-propylaziridine in a yield of 26%.

EXAMPLE 4

A mixture of 0.5 mmol of N-butylidenebutylamine, 1 mmol of ethyl diazoacetate, 0.015 mmol of di-μ-chlorotetrakis(cyclooctene)diiridium(I) [$Ir_2Cl_2$(cyclooctene)$_4$], and 0.5 ml of tetrahydrofuran was stirred at room temperature (25° C.) in an argon atmosphere for 3 hours to yield 1-butyl-2-ethoxycarbonyl-3-propylaziridine in a yield of 45%.

EXAMPLE 5

A mixture of 0.5 mmol of N-butylidenebutylamine, 1 mmol of ethyl diazoacetate, 0.015 mmol of di-μ-chlorotetrakis(cyclooctene)diiridium(I) [$Ir_2Cl_2$(cyclooctene)$_4$], and 0.5 ml of tetrahydrofuran was stirred at –5° C. in an argon atmosphere for 3 hours to yield 1-butyl-2-ethoxycarbonyl-3-propylaziridine in a yield of 77%.

EXAMPLE 6

A mixture of 0.5 mmol of N-butylidenebutylamine, 1 mmol of ethyl diazoacetate, 0.025 mmol of di-p-chlorobis(1,5-cyclooctadiene)diiridium(I) [$Ir_2Cl_2(cod)_2$], and 0.5 ml of tetrahydrofuran was stirred at –5° C. in an argon atmosphere for 3 hours. As a result, 1-butyl-2-ethoxycarbonyl-3-propylaziridine was obtained in a yield of 66%. Separately, small amounts of diethyl fumarate and diethyl maleate were formed as by-products in total yield of 19%.

EXAMPLE 7

The procedure of Example 6 was repeated, except that 0.5 mmol of N-butylidene-sec-butylamine was used instead of N-butylidenebutylamine, to yield 1-sec-butyl-2-ethoxycarbonyl-3-propylaziridine in a yield of 59%.

EXAMPLE 8

The procedure of Example 6 was repeated, except that 0.5 mmol of N-butylidene-tert-butylamine was used instead of N-butylidenebutylamine. As a result, 1-tert-butyl-2-ethoxycarbonyl-3-propylaziridine was obtained in a yield of 63%.

EXAMPLE 9

Using 0.5 mmol of N-(2-methylpropylidene)butylamine instead of N-butylidenebutylamine, the procedure of Example 6 was repeated to produce 1-butyl-2-ethoxycarbonyl-3-isopropylaziridine in a yield of 62%.

EXAMPLE 10

Using 0.5 mmol of N-(1-methylethylidene)butylamine instead of N-butylidenebutylamine, the procedure of Example 6 was repeated to produce 1-butyl-2-ethoxycarbonyl-3,3-dimethylaziridine in a yield of 36%.

EXAMPLE 11

The procedure of Example 6 was repeated, except that 0.5 mmol of N-benzylidenebutylamine was used instead of N-butylidenebutylamine, to yield 1-butyl-2-ethoxycarbonyl-3-phenylaziridine in a yield of 8%.

EXAMPLE 12

The procedure of Example 6 was repeated, except that 0.5 mmol of N-butylidenebenzylamine was used instead of N-butylidenebutylamine, to yield 1-benzyl-2-ethoxycarbonyl-3-propylaziridine in a yield of 36%.

EXAMPLE 13

Using 0.5 mmol of N-butylideneaniline instead of N-butylidenebutylamine, the procedure of Example 6 was repeated to produce 2-ethoxycarbonyl-1-phenyl-3-propylaziridine in a yield of 6%.

EXAMPLE 14

A small amount of a molecular sieve was added to a mixture of 0.5 mmol of n-butyraldehyde, 0.5 mmol of butylamine, 1 mmol of ethyl diazoacetate, 0.025 mmol of di-1-chlorobis(1,5-cyclooctadiene)diiridium(I) [$Ir_2Cl_2(cod)_2$], and 0.5 ml of tetrahydrofuran. The resulting mixture was stirred at −5° C. in an argon atmosphere for 3 hours to yield 1-butyl-2-ethoxycarbonyl-3-propylaziridine in a yield of 74%.

EXAMPLE 15

Using 0.5 mmol of sec-butylamine instead of butylamine, the procedure of Example 14 was repeated to yield 1-sec-butyl-2-ethoxycarbonyl-3-propylaziridine in a yield of 77%.

EXAMPLE 16

Using 0.5 mmol of tert-butylamine instead of butylamine, the procedure of Example 14 was repeated to produce 1-tert-butyl-2-ethoxycarbonyl-3-propylaziridine in a yield of 75%.

EXAMPLE 17

The procedure of Example 14 was repeated, except that 0.5 mmol of benzylamine was used instead of butylamine, to produce 1-benzyl-2-ethoxycarbonyl-3-propylaziridine in a yield of 39%.

Other embodiments and variations will be obvious to those skilled in the art, and this invention is not to be limited to the specific matters stated above.

What is claimed is:

1. A process for producing an aziridine compound of formula (5)

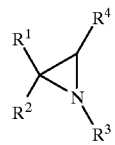

(5)

wherein $R^1$ and $R^2$ are each, identical to or different from each other, a hydrogen atom or a non-reactive organic group, or $R^1$ and $R^2$ may be combined to form a ring together with the adjacent carbon atom, $R^3$ is a hydrogen atom or a non-reactive organic group, and $R^4$ is —CN, —COOR$^5$ wherein $R^5$ is a hydrocarbon group or a heterocyclic group, or CONR$^6$R$^7$ wherein $R^6$ and $R^7$ are each, identical to or different from each other, a hydrogen atom, a hydrocarbon group, or a heterocyclic group, or $R^6$ and $R^7$ may be combined to form a ring together with the adjacent nitrogen atom, said process comprising the step of reacting a diazoacetic acid derivative of the formula $N_2CHR^4$ with a carbonyl compound of the formula $R^1R^2C=O$ and an amino-group-containing compound of the formula $R^3NH_2$ in the presence of an iridium compound to yield said aziridine compound.

2. The process of claim 1, wherein said carbonyl compound and said amino-group-containing compound are subjected to dehydration-condensation to form an imine of the formula $R^1R^2C=NR^3$ prior to their reaction with said diazoacetic acid derivative.

3. The process of claim 1, wherein said iridium compound is an organic iridium complex.

4. The process of claim 3, wherein said organic iridium complex is di-μ-chlorotetrakis(cyclooctene)diiridium (I).

5. The process of claim 3, wherein said organic iridium complex is di-μ-chlorotetrakis(ethylene)diiridium (I).

6. The process of claim 3, wherein said organic iridium complex is di-μ-chlorobis(1,5-cyclooctadiene)diiridium (I).

* * * * *